United States Patent
Deshpande et al.

(10) Patent No.: US 9,487,455 B2
(45) Date of Patent: *Nov. 8, 2016

(54) DEHYDROXYLATION OF CRUDE ALCOHOL STREAMS USING A HALOGEN-BASED CATALYST

(71) Applicant: DOW GLOBAL TECHNOLOGIES LLC, Midland, MI (US)

(72) Inventors: Raj Deshpande, Pune (IN); Paul Davis, Pune (IN); Vandana Pandey, Pune (IN); Nitin Kore, Solapur (IN)

(73) Assignee: Dow Global Technologies LLC, Midland, MI (US)

( * ) Notice: Subject to any disclaimer, the term of this patent is extended or adjusted under 35 U.S.C. 154(b) by 220 days.

This patent is subject to a terminal disclaimer.

(21) Appl. No.: 14/364,710

(22) PCT Filed: Dec. 5, 2012

(86) PCT No.: PCT/US2012/067836
§ 371 (c)(1),
(2) Date: Jun. 12, 2014

(87) PCT Pub. No.: WO2013/090076
PCT Pub. Date: Jun. 20, 2013

(65) Prior Publication Data
US 2014/0357921 A1    Dec. 4, 2014

Related U.S. Application Data

(60) Provisional application No. 61/570,960, filed on Dec. 15, 2011.

(51) Int. Cl.
*C07C 1/22* (2006.01)
*C07C 1/26* (2006.01)
*C07C 1/24* (2006.01)

(52) U.S. Cl.
CPC . *C07C 1/22* (2013.01); *C07C 1/24* (2013.01); *C07C 1/26* (2013.01); *C07C 2527/08* (2013.01)

(58) Field of Classification Search
None
See application file for complete search history.

(56) References Cited

U.S. PATENT DOCUMENTS

| | | | |
|---|---|---|---|
| 5,516,960 A * | 5/1996 | Robinson | C07C 1/20 568/671 |
| 2008/0216391 A1 | 9/2008 | Cortright et al. | |
| 2009/0299109 A1 | 12/2009 | Gruber et al. | |
| 2010/0069691 A1 | 3/2010 | Morschbacker | |
| 2010/0076233 A1 | 3/2010 | Cortright et al. | |
| 2010/0077655 A1 | 4/2010 | Bauldreay et al. | |

FOREIGN PATENT DOCUMENTS

| | | |
|---|---|---|
| WO | 2008/103480 A2 | 8/2008 |
| WO | 2013/090070 A1 | 6/2013 |
| WO | 2013/090071 A1 | 6/2013 |
| WO | 2013/090074 A1 | 6/2013 |

OTHER PUBLICATIONS

Bradbury, "The Mechanism of the Reaction between Glycerol and Hydriodic Acid" Journal of the American Chemical Society 1952 74 (11), 2709-2712.*
Arceo, Chem. Commun, 2009, vol. 23, p. 3357-3359.
Barue, Tetrahedron Letters, 1982, vol. 23, No. 13, p. 1365-1366.
Erlenmeyer, Studien iiber den Process der Einwirkung von Jodwasserstoff auf Glycerin Justus Liebigs Annalen Der Chemie, vol. 139, No. 2, p. 211-23.
Korshak, High Molecular weight compounds, 1950, p. 276-277.
Sarmah, Tetrahedron, 1989, vol. 45, No. II, p. 3569 to 3574.
Snyder, J. Am. Chem. Soc., 1955, vol. 77, p. 364-366.
Yang, ChemSusChem, 2012, vol. 5, p. 1218-1222.
Ziegler, Inorganic Chemistry, 2009, vol. 48, p. 9998-10000.
PCT/US2012/067836, Mar. 8, 2013, International Search Report and Written Opinion.
PCT/US2012/067836, Oct. 14, 2013, Response Written Opinion.
PCT/US2012/067836, Nov. 28, 2013, Written Opinion of the International Preliminary Examination Authority.
PCT/US2012/067836, Jan. 27, 2014, Amendment Under Rule 66.
PCT/US2012/067836, Mar. 31, 2014, International Preliminary Report on Patentability.

* cited by examiner

*Primary Examiner* — In Suk Bullock
*Assistant Examiner* — Jason Chong
(74) *Attorney, Agent, or Firm* — Dinsmore & Shohl LLP

(57) ABSTRACT

Crude alcohol streams are converted to olefins under reductive or non-reductive dehydroxylation conditions, in the presence of a halogen-based catalyst. The process includes autogenous gas pressure or a gas pressure from 1 psig (~6.89 KPa) to 2000 psig (~13.79 MPa), a temperature from 50° C. to 250° C., a liquid reaction medium, and a molar ratio of alcohol to halogen from 1:10 to 100:1.

6 Claims, No Drawings

DEHYDROXYLATION OF CRUDE ALCOHOL STREAMS USING A HALOGEN-BASED CATALYST

This application is a non-provisional application claiming priority from the U.S. Provisional Patent Application No. 61/570,960, filed on Dec. 15, 2011, entitled "DEHYDROXYLATION OF CRUDE ALCOHOL STREAMS USING A HALOGEN-BASED CATALYST," the teachings of which are incorporated by reference herein as if reproduced in full hereinbelow.

This invention relates generally to the field of dehydroxylation of crude glycerol. More particularly, it is a process to accomplish reductive or non-reductive dehydroxylation of crude alcoholstreams from biodiesel manufacture.

Crude glycerol is a product of various processes. Among these are biodiesel manufacture. The biodiesel process includes a transesterification (saponification) wherein sodium ethoxide must be neutralized. The result of this neutralization is a crude glycerol product that typically includes 80-85 weight percent (wt %) glycerol, 12-16 wt % water, 1-2 wt % salts, and up to 1 wt % methanol. These salts generally constitute sodium chloride, phosphate and other salts, along with some organics and otherwise unidentified color components. The salts must then be separated out before the glycerol is suitable for use or further processing. This purification adds to the cost of using such glycerol as a raw material. Furthermore, this process result produces more than one alcohol and also water, and separation of the methanol and water is also often considered necessary in order to obtain a desirably pure product.

Other processes, such as sugar hydrogenolysis, may result in crude streams that comprise more than one alcohol and also additional salts and/or water. Processes to successfully separate and purify these mixed and/or contaminated streams for further use have been sought from a variety of approaches.

For example, United States Patent Publication (US) 2010/0077655 discloses the conversion of water soluble oxygenated compounds derived from biomass into C4+ liquid fuel hydrocarbon compositions via numerous steps incorporating, for example, dehydration, hydrogenolysis, and condensation. The process is a multi-step one wherein a deoxygenation step is used for the formation of an oxygenate with the formula $C_{1+}O_{1-3+}$. These oxygenates comprise alcohols, ketones or aldehydes that can undergo further condensation reactions to form larger carbon number compounds or cyclic compounds. The catalysts proposed for the deoxygenation reaction are heterogeneous catalysts which consist of numerous metals and their combinations supported on a solid support. The support can be acidic supports, oxides, heteropolyacids, clays, and the like.

US 2010/0076233 discusses the conversion of oxygenated hydrocarbons to paraffins useful as liquid fuels. The process involves the conversion of water soluble oxygenated hydrocarbons to oxygenates, such as alcohols, furans, ketones, aldehydes, carboxylic acids, diols, triols, and/or other polyols, followed by the subsequent conversion of the oxygenates to olefins via dehydration. Subsequently the olefins are reacted with C4+ iso paraffins to convert to C6+ paraffins. The reactions are conducted in the presence of metal catalysts. The deoxygenation catalyst consists of a support with various metals deposited thereon, either singly or in combinations. The support is selected from carbon, metal oxides, heteropoly acids, clays and their mixtures. The oxygenated hydrocarbons may originate from any source, but are preferably derived from biomass.

US 2020/0069691 discloses a method for the production of one or more olefins from the residue of at least one renewable natural raw material. The patent discusses the formation of ethylene and propylene via dehydration of ethanol and propanol. The ethanol and propanol are, in turn, prepared from biomass via fermentation of sugar (ethanol) and from syngas derived via gasification of biomass.

US 2009/0299109 discusses renewable compositions derived from fermentation of biomass. Fermentation produces C2-C6 alcohols, which can be dehydrated to olefins. The C2-C6 alcohols can be derived from biomass via fermentation or chemical routes via catalytic hydrogenation. The dehydration of the alcohols is conducted in the presence of heterogeneous or homogeneous acidic catalysts.

US 2008/02191 discloses the conversion of oxygenate hydrocarbons to hydrocarbons, ketones and alcohols useful as industrial chemicals and liquid fuels, such as gasoline, jet fuel and diesel fuel. The process involves the conversion of mono-oxygenated hydrocarbons, such as alcohols, ketones, aldehydes, furans, carboxylic acids, diols, triols, and/or other polyols to C4+ hydrocarbons, alcohols and/or ketones, by condensation. The oxygenated hydrocarbons may originate from any source, but are preferably derived from biomass. The deoxygenation is conducted in the presence of a deoxygenation catalyst. The deoxygenation catalyst is a heterogeneous catalyst having one or more materials capable of catalyzing a reaction between hydrogen and the oxygenated hydrocarbon to remove one or more oxygens from the oxygenated hydrocarbon and form the alcohol(s). The catalyst comprises various metals on supports, such as oxides, heteropolyacids, carbons, clays, and mixtures thereof. The condensation reaction is catalyzed by acid catalysts, preferably heterogeneous, including inorganic acids.

WO 2008/103480 discusses the conversion of sugars and/or other biomass to produce hydrocarbons, hydrogen, and/or other related compounds. The process involves the formation of alcohols or carboxylic acid from biomass. These are converted to hydrocarbons via decarboxylation or dehydration, respectively, in the presence of hydrogen. The reactions are conducted in the presence of a metal or metal ion catalyst, or a base.

*Tetrahedron*, Vol. 45, No. 11, pp 3569-3574, 1989 discloses vicinal diols and compounds containing vicinal diols being converted to olefins in the presence of aluminum triiodide in stoichiometric quantities.

*Tetrahedron Letters*, Vol. 23, No. 13, pp 1365-1366, 1982 discloses cis and trans vicinal diols being converted into olefins in a one-step reaction with chlorotrimethylsilane and sodium iodide. The mole ratio of sodium iodide is greater than the stoichiometric requirement, which indicates that the reagents are stoichiometric in nature.

*Inorganic Chemistry*, Vol. 48, pp 9998-10000, 2009 discloses methyltrioxorhenium (MTO) catalyzing the conversion of epoxides and vicinal diols to olefins with dihydrogen ($H_2$) as the reductant.

*J. Am. Chem. Soc.*, Vol. 77, pp 365, 1955 discloses vicinal dihalides converted to olefins by reaction with iodide ion. The reaction is stoichiometric in the iodide and the starting materials are dihalides.

*Chem. Commun.*, pp 3357, 2009 discloses the conversion of diols and polyols to olefins in the presence of formic acid.

In one aspect, this invention is a process for preparing an olefin comprising subjecting a crude alcohol stream including an alcohol selected from glycerol, propylene glycol, ethylene glycol, and combinations thereof, further containing an amount of at least one contaminant, to dehydroxylation conditions in the presence of a halogen-based catalyst containing at least one halogen atom, which conditions include a reductive or a non-reductive gas, at a pressure of from 1 pound per square inch gauge (psig) (~6.89 kilopascals (KPa)) to 2000 psig (~13.79 megapascals (MPa)), a temperature within a range of from 50 degrees Celsius (° C.) to 250° C., a liquid reaction medium, and a ratio of moles of the alcohol to moles of halogen atoms ranging from 1:10 to 100:1; such that at least one olefin is formed and the amount of the at least one contaminant is reduced.

A particular feature of the present invention is use of a halogen-based catalyst. As defined herein, a halogen-based catalyst contains at least one halogen atom and ionizes at least partially in an aqueous solution by losing one proton. It is important to note that the definition of halogen-based is applied to the catalyst at the point at which it catalyzes the dehydroxylation of the crude alcohol stream. Thus, it may be formed in situ in the liquid reaction medium beginning with, for example, a molecular halogen, e.g., molecular iodine ($I_2$), or may be introduced into the reaction as a halide acid, for example, as pre-prepared HI. Non-limiting examples include molecular iodine ($I_2$), hydroiodic acid (HI), iodic acid ($HIO_3$), lithium iodide (LiI), and combinations thereof. The term "catalyst" is used in the conventionally understood sense, to clarify that the halogen-based compound takes part in the reaction but is regenerated thereafter and does not become part of the final product. The halogen-based catalyst is at least partially soluble in the liquid reaction medium.

For example, in one non-limiting embodiment where HI is selected as the halogen-based catalyst, it may be prepared as it is frequently prepared industrially, i.e., via the reaction of $I_2$ with hydrazine, which also yields nitrogen gas, as shown in the following equation.

$$2I_2 + N_2H_4 \rightarrow 4HI + N_2 \quad \text{[Equation 1]}$$

When performed in water, the HI must be distilled. Alternatively, HI may be distilled from a solution of NaI or another alkali iodide in concentrated hypophosphorous acid. Another way to prepare HI is by bubbling hydrogen sulfide steam through an aqueous solution of iodine, forming hydroiodic acid (which must then be distilled) and elemental sulfur (which is typically filtered).

$$H_2S + I_2 \rightarrow 2HI + S \quad \text{[Equation 2]}$$

Additionally, HI can be prepared by simply combining $H_2$ and $I_2$. This method is usually employed to generate high purity samples.

$$H_2 + I_2 \rightarrow 2HI \quad \text{[Equation 3]}$$

Those skilled in the art will be able to easily identify process parameters and additional methods for preparing HI and/or other reagent falling within the scope of the invention. It is noted that sulfuric acid will not generally work for preparing HI as it will tend to oxidize the iodide to form elemental iodine.

As used herein the term "crude alcohol stream" is used to define the material being converted by the action of the catalyst in the presence of the gaseous hydrogen under the reductive dehydroxylation conditions. This material includes the alcohol or mixture thereof (for example, glycerol, ethylene glycol, propylene glycol, or a combination thereof such as might result from, for example, a sugar hydrogenolysis process) and also at least one contaminant. As used herein, the term "contaminant" refers to any material included with the crude alcohol stream, other than one of the listed alcohols, in its form as a product of a manufacturing process, including, for example, biodiesel production or saponification of fatty oils with caustics. Such contaminants may include, but are not necessarily limited to, water; oils; salts, such as alkali metal chlorides, e.g., sodium chloride; alkali metal phosphates, e.g., potassium phosphate; organics, such as methanol; and combinations thereof. While there is no required minimum or maximum of the amount of contaminants present in the crude alcohol stream for application to the present invention, in practical application it is typical for such contaminants to be present (prior to reduction via the present invention) in a total amount ranging from 5 to 25 wt %, more typically from 15 to 20 wt %, based on the total crude alcohol stream. This includes but is not limited to water, which generally represents the majority of the total contaminants.

In practicing the present invention the crude alcohol stream and the catalyst are desirably proportioned to optimize dehydroxylation of the crude alcohol stream. Those skilled in the art will be aware without further instruction of conventional ways to determine such proportions, but generally a ratio of moles of material (the crude alcohol stream) to moles of halogen atoms ranging from 1:10 to 100:1 is preferred. More preferred is a molar ratio ranging from 1:1 to 100:1; still more preferably from 4:1 to 27:1; and most preferably from 4:1 to 8:1. Alteration of the proportion of the catalyst to the crude alcohol stream will alter the selectivity and conversion of products, but in general a starting crude alcohol stream, which contains glycerol, ethylene glycol, propylene glycol, or a combination thereof, may be converted predominantly to the corresponding olefin(s) and, in many cases, have at least a portion of contaminants removed, via application of the present invention.

Temperature parameters employed in the invention may vary within a range of from 50° C. to 250° C., but are preferably from 100° C. to 210° C. Those skilled in the art will be aware that certain temperatures may be preferably combined with certain molar ratios of crude alcohol stream and catalyst to obtain optimized olefin yield. For example, a temperature of at least 180° C. combined with a molar ratio of crude alcohol stream to halogen atoms of 6:1 may result, in some embodiments, in especially desirable yields of olefin(s). Other combinations of temperature and ratio of moles of material to moles of halogen atoms may also yield desirable results in terms of conversion of material and selectivity to desired alkenes. For example, with an excess of HI, temperature may be varied especially within the preferred range of 100° C. to 210° C., to obtain a range of conversion at a fixed time, e.g., 3 hours. Processing for a longer time at lower temperature is another embodiment. Those skilled in the art will be aware that alteration of any parameter or combination of parameters may affect yields and selectivities achieved, and that routine experimentation to identify optimized parameters will be, as is typical, necessary prior to advancing to commercial production.

In certain particular embodiments the conditions may also include a reaction time, desirably within a range of from 1 hour to 10 hours. While a time longer than 10 hours may be selected, such may tend to favor formation of byproducts such as those resulting from a reaction of the produced olefin, e.g., propylene or ethylene, with one or more of the crude alcohol stream constituents. Byproduct formation may be more prevalent in a batch reactor than in a continuous process, although either type of process may be employed. Conversely, a time shorter than 1 hour may reduce olefin yield as well as extent of contaminant removal.

The inventive process may be carried out as either a reductive dehydroxylation or a non-reductive dehydroxylation. In the case of a reductive dehydroxylation, gaseous hydrogen may be employed in essentially pure form as the reductant, but also may be included in mixtures further comprising, for example, carbon dioxide, carbon monoxide, nitrogen, methane, and any combination of hydrogen with one or more the above. The hydrogen itself may therefore be present in the atmosphere, generally a gas stream, in an amount ranging from 1 weight percent (wt %) to 100 wt %.

Where a non-reductive dehydroxylation is desired, the atmosphere/gas stream is desirably substantially or, preferably, completely hydrogen-free. As defined herein, "substantially free" means that the indicated gas may be present in an amount up to 2 wt %. In this case other gases, including but not limited to nitrogen, carbon dioxide, methane, and combinations thereof, may be employed. Any constituent therefore may be present in amounts ranging from 1 wt % to 100 wt %, but the total atmosphere is desirably at least 98 wt %, preferably 99 wt %, and more preferably 100 wt %, hydrogen-free.

The reductive (hydrogen-containing) or non-reductive atmosphere is useful in the present invention at a gas pressure sufficient to promote formation of the olefin. The applied pressure is desirably from 1 psig (~6.89 KPa) to 2000 psig (~13.79 MPa), and preferably from 50 psig (~344.5 KPa) to 200 psig (~1.38 MPa). A gas pressure within the above ranges, especially the preferred range, is often favorable for efficient conversion of molecular halide to corresponding acid iodide. In many embodiments gas pressures in excess of 2000 psig (~13.79 MPa) provide little or no discernible benefit and may simply increase cost of the process. Autogenous pressure may also be employed, particularly in the case of a substantially non-reductive dehydroxylation.

The conversion may be accomplished using many of the equipment and overall processing parameter selections that are generally known to those skilled in the art. Depending in part upon other processing parameters selected as discussed hereinabove, it may be desirable or necessary to include a liquid reaction medium. The crude alcohol stream may function as both the compound to be converted and the liquid reaction medium wherein the conversion will take place, or if desired, an additional solvent such as water, acetic acid, or another organic may be included. Acetic acid may help to dissolve the halogen formed as part of the catalytic cycle and act as a leaving group, thereby facilitating the cycle, but because esterification of the polyol occurs, water is liberated. Conversely, while water may be effectively selected, particularly in the case of the non-reductive hydroxylation embodiment, selectivity may be thereby sacrificed. Organic solvents may be helpful in removing the accumulated water during the course of the reaction. In one embodiment, a carboxylic acid that contains from 2 carbon atoms to 20 carbon atoms, preferably from 8 carbon atoms to 16 carbon atoms, may be selected as a liquid reaction medium. Polyols and dialkyl ethers may also be selected.

It is noteworthy that the inventive process may be accomplished in either one or two steps. If a two step process is desired, the basic reaction may first be conducted under stochiometric conditions. In this case a relatively low temperature in the range of from 50° C. to 120° C. and the relatively low (less than 50 psig, ~0.34 MPa) pressure of hydrogen are employed. This protocol helps to avoid the formation of byproducts. The regeneration of $I_2$ to HI may then be undertaken in a second step at a higher temperature, in the range of from 180 to 210° C., and under a similar hydrogen pressure.

EXAMPLES

General Experimental Procedure

Use a 300 milliliter (mL), High Pressure HASTELLOY™ C-276 Parr reactor with a glass insert as a reaction vessel. Charge 90 mL of acetic acid (S.D. Fine-Chem Ltd.) into the reactor. Add a known amount of crude glycerol (glycerol content 84 wt %, water 14 wt %, methanol 1 wt % and dissolved salts (sodium chloride, sodium phosphate, etc., estimated amount 1 wt %, pH 6) to the acetic acid. Add 4 mL of a 55% (weight/weight) aqueous solution of HI (0.029 moles) (Merck) or 3.73 gram (g) $I_2$ to the reactor, then close the reactor and mount it on a reactor stand. Flush void space within the reactor two times with gaseous $N_2$ (200 psig (~1.38 MPa). Feed $H_2$ into the reactor up to a pressure of 50 psig (0.345 MPa) and heat reactor contents, with stirring at a rate of 1000 revolutions per minute (rpm) up to a temperature of 210° C. Add sufficient additional $H_2$ to the reactor to increase pressure within the reactor up to 1000 psig (~6.89 MPa). After 45 minutes of reaction time, remove a sample of vapor phase within the reactor using a gas sampling vessel. Analyze the sample via gas chromatography (GC) (Agilent 7890 with two thermal conductivity detectors (TCDs) and one flame ionization detector (FID)). Use a PoraPlot™ Q (Varian™ CP7554) column to separate carbon dioxide ($CO_2$), olefins and alkanes. Use a CP Wax (Varian™ CP7558) column to separate oxygenates and a molecular sieve (Molsieve) (Varian™ CP7539) column to separate hydrogen, nitrogen and lower hydrocarbons. The reaction is continued in this fashion for a desired period of time. Based upon the vapor phase composition, calculate the mole percent (mol %) of polyol present in the crude alcohol stream corresponding to the olefin formed. The gas liquid phase is analyzed on GC (Liquid sample GC analysis is carried out using an Agilent 7890 gas chromatogram fitted with a split/splitless capillary injector with a split injector liner, tapered, low pressure drop with glass wool and flame ionization detector. The injection volume used is 1 microliter (μL) and split ratio is 1:20. The GC method uses a combined DB 1701 and HP5 GC columns Samples are injected using an Agilent 7683B auto injector.

Calculate mole percent (mol %) conversion of material to olefin from vapor phase composition data according to the following equation:

$$\text{mole \%} = \left[ \frac{\frac{\text{vol \%}}{100} \times \frac{\text{total pressure}}{14.7} \times \frac{\text{volume of gas}}{22400}}{\text{moles of material}} \right] \times 100 \quad \text{[Equation 4]}$$

Comparative Example A

Using the above General Experimental Procedure with 0.029 moles of glycerol, 0.004 moles of HI, a temperature of 210° C. and a time of 5 hours, effect a 100% conversion of the glycerol with 78 and 22% selectivity to propylene and carbon dioxide, respectively.

Example 1

Replicate Comparative Example A, but substitute 0.02 moles of crude glycerol for the glycerol, and the time to 6 hours. This Example 1 effects 100% conversion of the crude glycerol with a product stream selectivity of 80% propylene, 4% propane, and 16% $CO_2$, respectively.

Example 2

Replicate Comparative Example A, but substitute 0.03 moles of crude glycerol for the glycerol, and change time to 6.5 hours in the absence of hydrogen. This Example 2 effects 59% conversion of the crude glycerol with a product stream selectivity of 38% propylene, 49% $CO_2$ and 13% CO, respectively.

Example 3

Replicate Comparative Example A, but substitute 0.031 moles of triacetin for the glycerol, and change time to 6.5 hours. This Example 3 effects 100% conversion of the triacetin with a product stream selectivity of 84% propylene, 12% $CO_2$ and 4% CO, respectively.

Example 4

Replicate Example 3, but substitute 0.03 moles of triacetin for the glycerol, and change time to 6 hours. This Example 4 effects 24% conversion of the triacetin with a product stream selectivity of 96% propylene, 2% $CO_2$ and 2% CO, respectively.

The invention claimed is:

1. A process for preparing an olefin comprising
performing hydrogenolysis of sugar or saponification of at least one fatty oil with caustic to obtain a crude alcohol stream,
subjecting the crude alcohol stream to dehydroxylation in presence of a liquid reaction medium and a halogen-based catalyst selected from the group consisting of iodine ($I_2$), hydrogen iodide (HI), and combinations thereof, to form at least one olefin and an amount of at least one contaminant is reduced,
wherein the crude alcohol stream is selected from the group consisting of glycerol, propylene glycol, ethylene glycol, and combinations thereof,
wherein the crude alcohol stream further comprises a total amount of 5 weight percent to 25 weight percent, based on weight of the crude alcohol stream as a whole, of at least one contaminant selected from the group consisting of alkali metal chlorides, alkali metal phosphates, water, oils, and combinations thereof,
the dehydroxylation conditions comprising
a reductive or a non-reductive gas,
a gas pressure ranging from 1 psig to 2000 psig, or an autogenous pressure,
a temperature ranging from 50° C. to 250° C.,
a ratio of moles of the alcohol to moles of the iodine atoms in the halogen-based catalyst ranging from 4:1 to 27:1.

2. The process of claim 1, wherein the gas pressure is from 50 psig to 500 psig.

3. The process of claim 1, wherein the temperature is within a range of from 100° C. to 210° C.

4. The process of claim 1, wherein the ratio of moles of the alcohol to moles of the iodine atoms ranges from 4:1 to 8:1.

5. The process of claim 1, wherein the halogen-based catalyst is hydrogen iodide (HI).

6. The process of claim 1, wherein the dehydroxylation is conducted as a two-step process comprising a first step and a second step,
wherein the first step comprises a partial dehydroxylation under conditions including a first gas pressure ranging from 1 psig to 50 psig and a first temperature ranging from 50° C. to 120° C., and
wherein the second step comprises continuing the dehydroxylation under conditions including a second gas pressure ranging from 1 psig to 50 psig and a second temperature ranging from 180° C. to 210° C.

* * * * *